United States Patent [19]

Miller et al.

[11] Patent Number: 4,552,513
[45] Date of Patent: Nov. 12, 1985

[54] MULTIPLE PISTON PUMP CONTROL

[75] Inventors: Leslie A. Miller, San Jose; Thomas J. McCall, Fremont, both of Calif.

[73] Assignee: Spectra-Physics, Inc., San Jose, Calif.

[21] Appl. No.: 472,668

[22] Filed: Mar. 7, 1983

[51] Int. Cl.⁴ .......................... F04B 49/06; F04B 3/00
[52] U.S. Cl. ........................................ 417/18; 417/53; 417/265
[58] Field of Search .................. 417/18, 22, 53, 42, 417/265; 128/DIG. 13

[56] References Cited

U.S. PATENT DOCUMENTS

| | | | |
|---|---|---|---|
| 3,847,507 | 11/1974 | Sakiyama | 417/22 |
| 4,080,966 | 3/1978 | McNally | 128/DIG. 13 |
| 4,180,375 | 12/1979 | Magnussen | 417/22 |
| 4,225,290 | 9/1980 | Allington | 417/18 |
| 4,326,837 | 4/1982 | Gilson | 417/42 |
| 4,359,312 | 11/1982 | Funke | 417/18 |
| 4,389,163 | 6/1983 | Magnussen | 417/2 |

Primary Examiner—William L. Freeh
Attorney, Agent, or Firm—Donald C. Feix

[57] ABSTRACT

A multiple piston assembly pump of the kind which provides an overlap between the flow output of the piston assemblies during a portion of the strokes of the piston assemblies incorporates a method and apparatus for reducing pulsations in the flow during the time when the pump is changing over from one piston pumping to the other piston pumping. A first fast control loop responds to pump output pressure and is operatively associated with a second slow control loop which responds to average pump speed. A sudden pump speed change is detected, and the pump is run in a constant pressure mode until the speed returns to normal.

4 Claims, 18 Drawing Figures

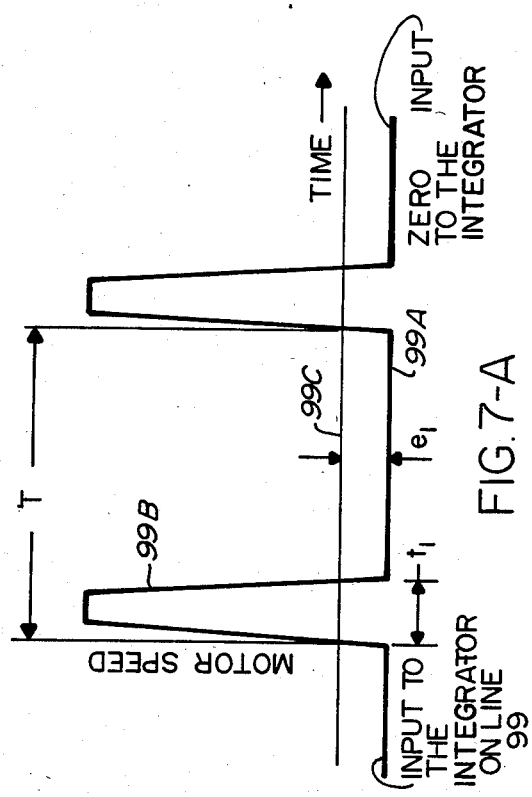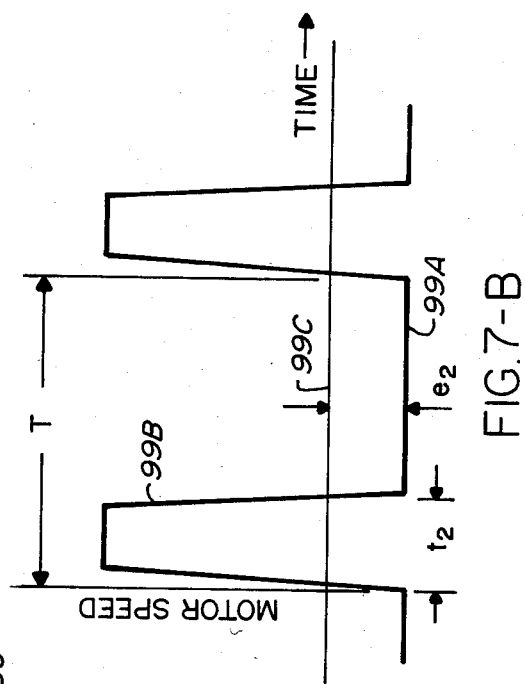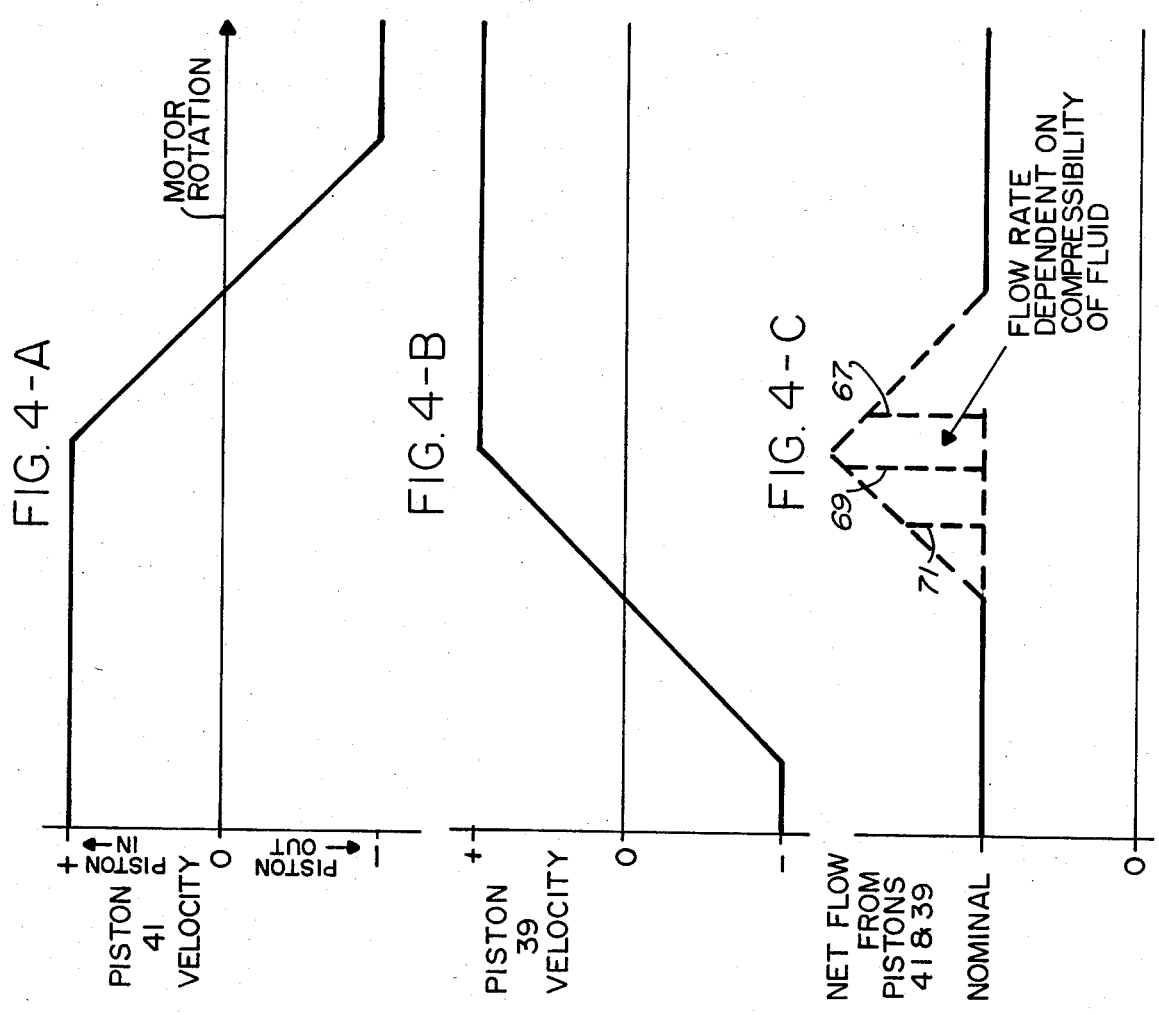

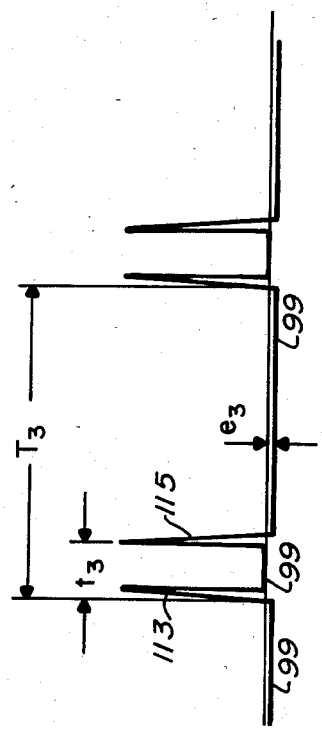
FIG. 8-A
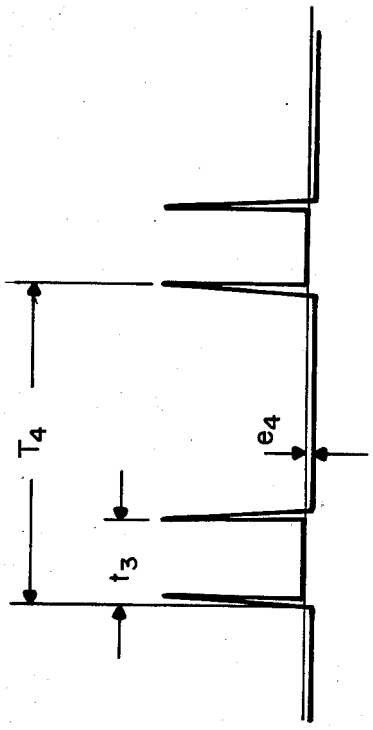
FIG. 8-B
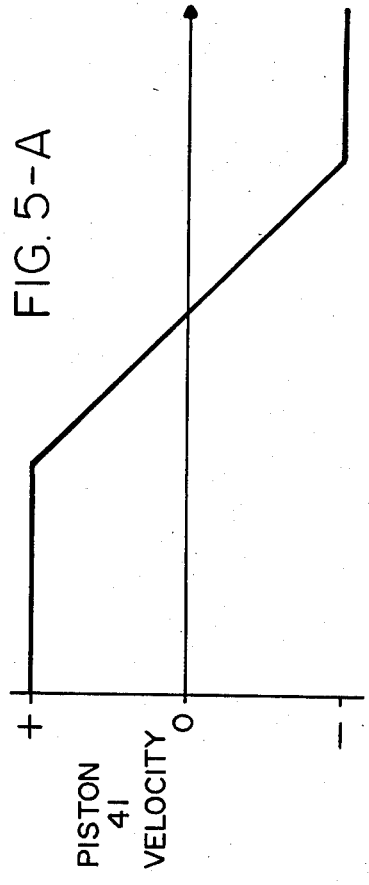
FIG. 5-A
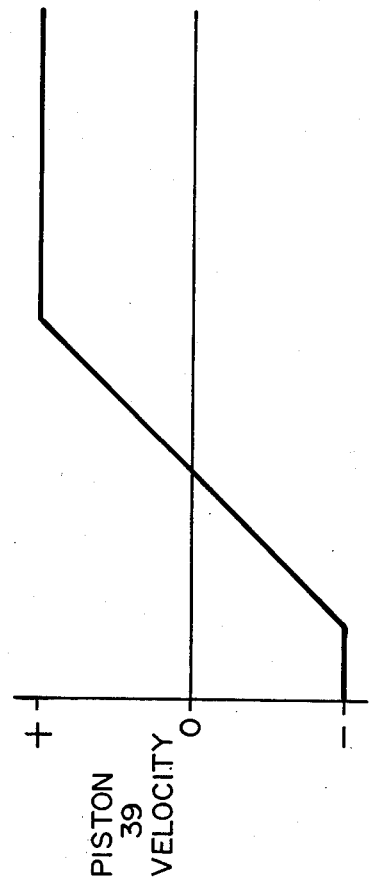
FIG. 5-B
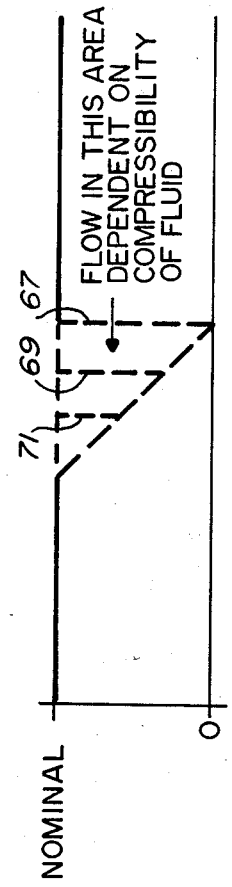
FIG. 5-C

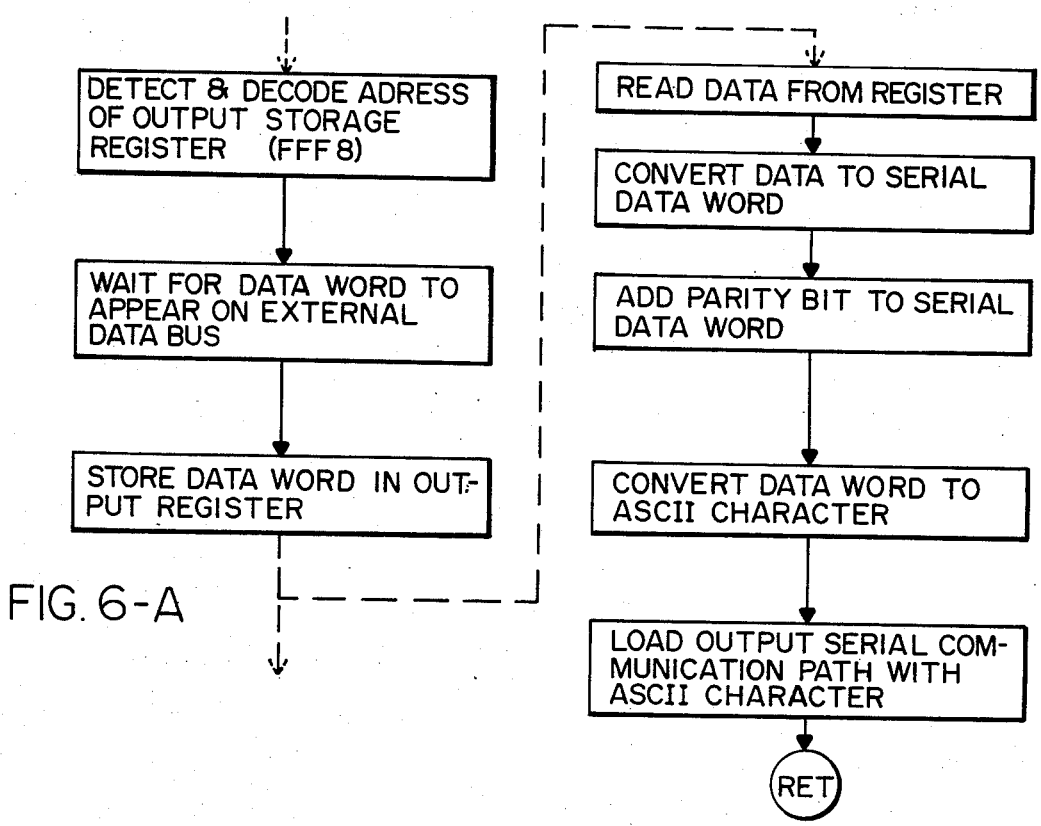
FIG. 6-A
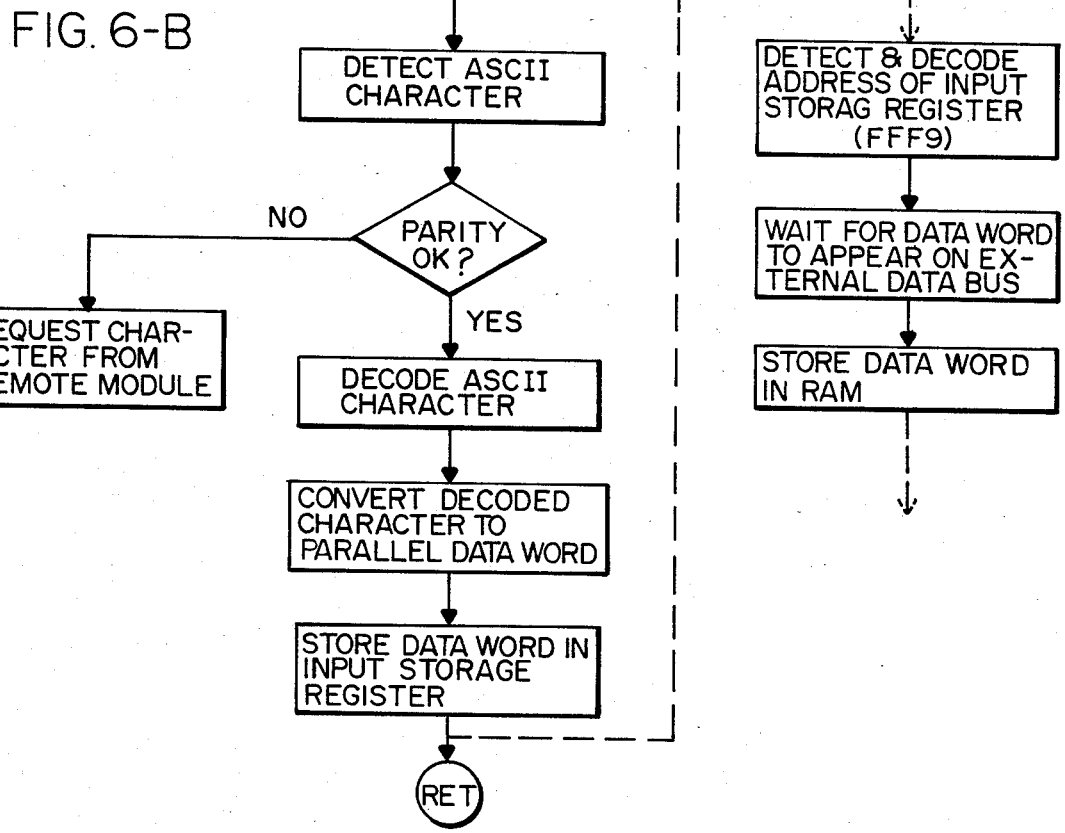
FIG. 6-B

MULTIPLE PISTON PUMP CONTROL

BACKGROUND OF THE INVENTION

This invention relates to methods and apparatus for reducing pulsations in the flow produced by a multiple piston assembly pump of the kind which provides an overlap between the flow output of the piston assemblies during a portion of the strokes of the piston assemblies.

This invention relates particularly to a pump used for liquid chromatography.

The present invention has particular application to a dual piston pump of the kind disclosed in U.S. Pat. No. 4,352,636 issued Oct. 5, 1982 and assigned to the same assignee as the present application; and this U.S. Pat. No. 4,352,636 is hereby incorporated by reference in this application.

Pulseless flow of the liquid supplied to a column for liquid chromatography is desirable to permit the column to achieve greater resolution of peaks. Pulseless flow also permits the detector to operate at a more sensitive range (to detect smaller peaks), and pulseless flow is less restrictive on an integrator used in liquid chromatography apparatus.

A constant flow over a long term is necessary for repeatability of the retention times of the chromatogram peaks and is a factor in the area of the peak.

As disclosed in U.S. Pat. No. 4,352,636, the control for a dual piston pump of this kind has included two control loops—a first fast responding control loop for controlling the pressure that the pump is pumping and a second slow responding control loop for producing a slow responding pressure set point for monitoring average pump speed.

The dual control loop theory works with any multiple piston pump, but there can be a problem in achieving proper control during the time when the pump is changing over from one piston pumping to the other piston pumping. During the piston changeover, the motor speed is not a good indicator of flow. The duration of the changeover period can vary with differences in the compressibility of different solvents and with errors and irregularities in the external system (such as, for example, variability in closing time of check valves, small imperfections in the cams driving the pistons, etc.). At this point in the cycle of operation, there can be a sudden pump speed change, it is desirable to run the pump at a substantially constant pump output pressure until the pump speed returns to the normal speed existing prior to the sudden speed change. If the response rate of the slow responding control loop is made slow enough to hold the pressure constant during this changeover period, then the response rate of this slow responding control loop must also be slow in responding both to the system solvent changes and to initial start-up, and this is undesirable.

It is a primary object of the present invention to detect a sudden pump speed change during the time of piston changeover and to run the pump in a constant pressure mode until the speed returns to normal.

In a specific embodiment of the present invention this object is accomplished by forcing the input of an integrator located in the slow responding control loop to zero in response to and during the duration of the time involved between the detection of the sudden pump speed change and the return to the normal pump speed.

By forcing the integrator to hold the pressure constant during the changeover period, the second slow control loop can be provided with a much faster response time than would be the case than if the integrator did not hold the pressure constant at this point in the cycle. This permits the second slow responding control loop to provide better response to system solvent changes and initial start-up, and this is an important advantage in the overall pump control.

SUMMARY OF THE INVENTION

A pump control for reducing pulsations in the flow produced in a multiple piston assembly pump of the kind which provides an overlap between the flow output of the piston assemblies during a portion of the strokes of the piston assemblies comprises a first relatively fast responding control loop for controlling the pump in response to pump output pressure and a second relatively slow responding control loop for controlling the pump in response to average pump speed.

The pump control method and apparatus of the present invention include compensation means for detecting a sudden pump speed change and for holding a substantially constant pump output pressure until the pump speed returns to the normal speed existing prior to the sudden speed change. Constant pressure is a means to constant volumetric flow during the changeover when motor speed is not a good indication of flow. This mode of operation compensates for varying changeover periods caused by differences in the compressibility of different solvents and the external system.

In a specific embodiment of the present invention having two pistons, both pistons are driven through a gear and cam mechanism from a common motor driver. The speed of the motor driver is responsive to the output signal of a pressure error amplifier.

The pressure error amplifier has two inputs. One input is from a pressure amplifier and its transducer and the other input is from the slow responding control loop.

The input from the slow loop comes from the output of an integrator, and the input to the integrator is normally the output of a flow error amplifier which determines the error between the flow rate as set at the control panel and the instantaneous speed of the motor driver.

In normal operation, the slow responding loop will eventually find a point at which there is no average error between the set point speed and the actual speed, and the average input to the integrator will at that point be zero.

The fast responding control loop includes a pressure transducer at the outlet of the pump and a pressure amplifier for supplying a signal to the pressure error amplifier.

A switch is located in the line between the flow error amplifier and the integrator of the slow control loop, and this switch is activated in response to the detection of a sudden pump speed change to force the input to the integrator to zero. The switch is deactivated in response to a detection of the return of the pump speed to the normal speed existing prior to the sudden speed change.

The control thus uses motor speed for control of the flow when it is a good indication of flow and holds constant pressure during the changeover. This compensates for varying changeover periods caused by differences in the compressibility of different solvents and the external system.

Pump control apparatus and methods which incorporate the structure and techniques described above and which are effective to function as described above constitute specific objects of this invention.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTION OF THE DRAWINGS

FIG. 2 illustrates how the components are identified by retention time and how the size of the components are quantitated according to area under the peaks.

FIGS. 4A through 4C are diagrams showing the relationship of piston velocity to motor rotation for a multiple piston pump of the kind shown in FIG. 3 in which the pistons produce a positive overlap and an increased flow output at a certain point in the operation of the pump. FIG. 4A shows the plot of piston velocity versus motor rotation for a damper piston. FIG. 4B shows the plot of piston velocity versus motor rotation for the compression piston.

FIG. 4C shows a plot of the net flow from both pistons versus motor rotation and illustrates how the compressibility of the fluid affects the net flow at the point of overlap between the output of the two pistons in the pump construction shown in FIG. 3.

FIGS. 5A through 5C are plots of piston velocity versus motor rotation (like the plots shown in FIGS. 4A through 4C) but in FIGS. 5A through 5C the plots are shown for a pump of the kind in which there is a negative overlap between the piston output, and the speed of rotation of the pump must be increased (rather than decreased as in FIG. 4) to maintain a constant output flow in the area of overlap.

FIGS. 6, 6A and 6B is a diagram showing the components of a dual loop control circuit for controlling motor speed to obtain constant flow with the pump of the present invention.

FIGS. 7A and 7B are diagrams showing motor speed versus time for solvents of two different compressibilities and these two diagrams show the effect of pulse and width and motor speed. These two diagrams show the effect of pulse width on the error between average motor speed and motor speed in the smooth portion of the pump stroke. FIGS. 7A and 7B are plots of the pulse width that would be produced with the FIG. 3 type pump using the FIG. 6 control circuit but without a compensation circuit portion of the FIG. 6 control circuit. The compensation circuit in FIG. 6 is that part of the circuit enclosed by the dash line in FIG. 6 and labeled "compensation circuit".

FIGS. 8A and 8B are plots like FIGS. 7A and 7B but showing the effect of including the compensation circuit in the FIG. 6 control circuit.

FIG. 9 illustrates the target pressure output signal without the compensation circuit. FIG. 10 illustrates the output of the target pressure output signal of the integrator when the compensation circuit is utilized in the FIG. 6 control circuit.

DETAILED DESCRIPTION OF THE PREFERRED EMBODIMENTS

Figure 1:
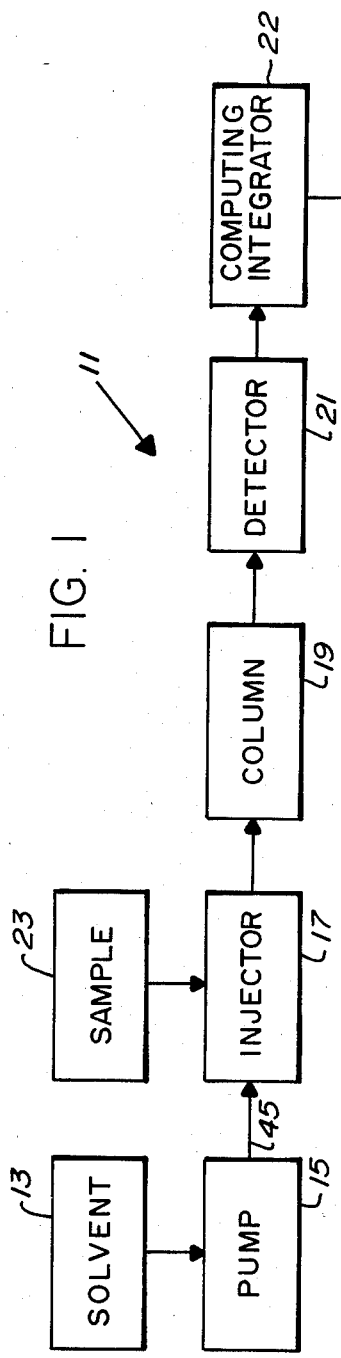
FIG. 1 is a block diagram showing a liquid chromatograph system constructed in accordance with one embodiment of the present invention.

A block diagram of a liquid chromatograph system and apparatus constructed in accordance with one embodiment of the present invention is indicated generally by the reference numeral 11 in FIG. 1.

As illustrated in FIG. 1 the liquid chromatograph apparatus 11 comprises a solvent reservoir 13 which feeds a solvent composition into a pump 15. The pump 15 provides a constant flow through an injector 17 and column 19 to a detector 21. The sample 22 to be analyzed is introduced into the system 11 through the injector 17. It passes on to the column 19 where it is separated into its constituent parts. The constituent parts then pass through the detector 21. The various constituents of the sample produce an analog signal in the detector in a manner illustrated in FIG. 2. These signals are passed on to a computing integrator 23 for quantitazation and plotting. The computing integrator 23 produces a chromatogram plot 25.

Figure 2:
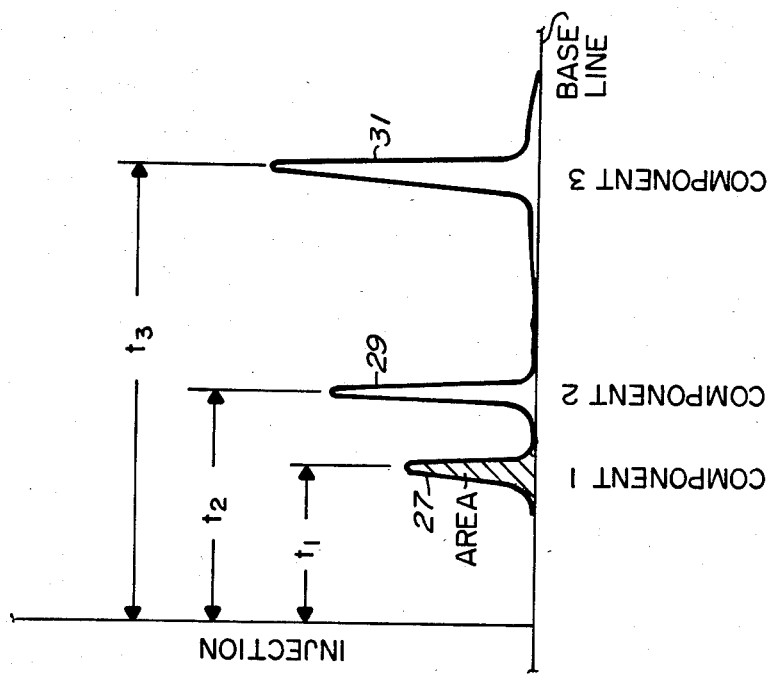
FIG. 2 is a typical chromatograph showing three sample components.

With specific reference now to FIG. 2, the various components of the sample are detected as separate peaks 27, 29 and 31. These peaks occur at different retention times corresponding to the makeup of the different components, and the area under each peak is an indication of the quantity of that component.

To obtain effective analysis the peaks 27, 29, 31, etc. must be well separated and the various retention time and areas of the peaks must be reproducible.

To obtain the desired separation of peaks, reproducibility of retention times and reproducibility of areas, it is very important that the flow produced by the pump 15 be constant and accurate; that is, the flow produced by the pump 15 must have a minimum of sharp variation or pulses which could blur the separation between the peaks and/or produce large noise spikes with respect to the base line as illustrated in FIG. 2.

Pulses in the pump output can produce noise spikes on each revolution of the pump which could interfere with proper interpretation of the chromatogram.

The pump elevates the solvent pressure, producing a constant, pulseless flow which passes into the injector 17.

The present invention utilizes a multiple piston pump which provides an overlap in the flow output of the two pistons.

In a preferred embodiment of the present invention the flow overlap is produced as a positive flow overlap so that the speed of rotation of the pump can be slowed down at this critical period in the cycle of operation of the pump, but the present invention also can utilize a multiple piston pump in which a negative flow overlap is produced and in which the speed of rotation of the pump is increased, under control of the control circuit, at this period in the cycle of operation.

Figure 3:
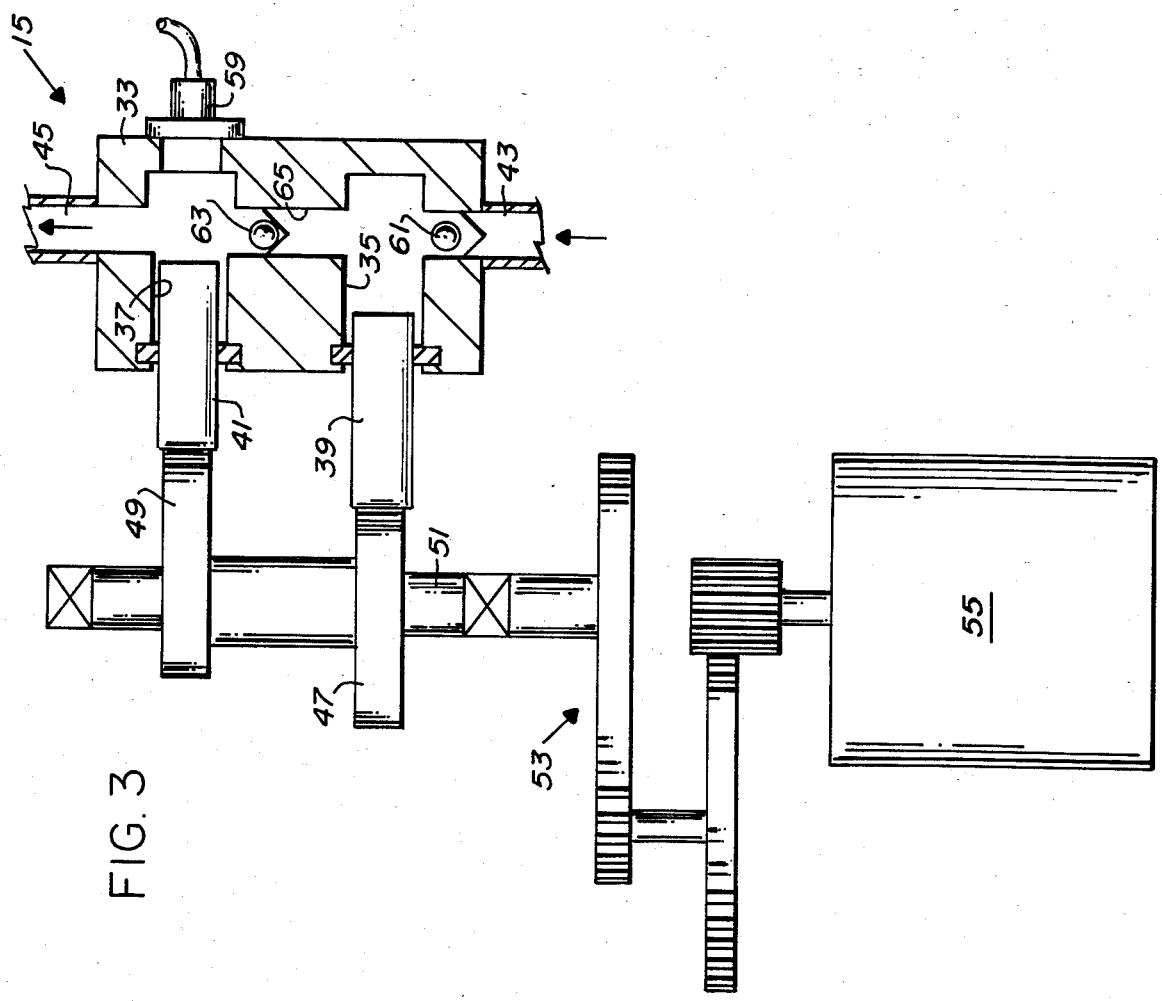
FIG. 3 is a schematic diagram showing one embodiment of the multiple piston pump wich can be used in the present invention.

FIG. 3 illustrates one preferred embodiment of the pump of the present invention in which the pump 15 comprises a cylinder housing 33. Cylinder housing 33 comprises a pressurization piston chamber 35 and a damper piston chamber 37. A pressure piston 39 reciprocates within the pressure chamber 35 and a damper piston 41 reciprocates within the damper cylinder 37. The pump shown in FIG. 3 is generally like that shown in U.S. Pat. No. 4,352,636 referred to above and incorporated by reference in this application.

The pump 15 includes the solvent inlet 43 and a solvent outlet 45.

The pistons 39 and 41 are driven by respective cams 47 and 49, and the cams 47 and 49 are mounted for rotation on a drive shaft 51.

The drive shaft 51 is driven by a gear train 53 from a stepper motor 55.

The speed of rotation of the stepper motor 55 is controlled by control circuit 57 shown in FIG. 6 (to be described in more detail below).

A pressure transducer 59 is associated with the solvent outlet 45.

Check valves 61 and 63 are associated with the respective solvent inlet 43 and the passageway 65 between the chambers 35 and 37.

The pump 15 shown in FIG. 3 can produce either a positive flow overlap or a negative flow overlap at the crossover point between the flow produced by the pistons 39 and 41, depending upon the specific cam contours of the cams 47 and 49.

It is possible, with any one constant solvent composition to grind the cam contours of the cams 47 or 49 to produce an essentially pulseless flow output at a given pressure level. However, even in that instance, compressibility varies with pressure level, and some regulation of the speed of rotation of the shaft 51 is desirable. When different solvents or different solvent compositions are used, the compressibility can vary widely, and provision for the control of the speed of rotation of the shaft 51 (to minimize pulses in the flow output) becomes even more critical.

FIGS. 4A through 4C graphically illustrate the relationship between the piston velocities for the two pistons 39 and 41 and the resulting net flow output from the output line 45 at the point of overlap in the flow between these two pistons.

Thus, FIG. 4A illustrates the velocity of piston 41 and shows it slowing down at the end of its stroke.

FIG. 4B shows the velocity of piston 39 and show it speeding up at the beginning of its stroke, which occurs just slightly prior in time to the ending of the pressure stroke of piston 41.

The cam contour provided for the piston plot showing FIGS. 4A and 4B produces a net positive flow pulse in the output of the pump 15 at the point of overlap of the two pistons, if the speed of rotation of the shaft 51 is maintained constant. This net positive flow pulse is illustrated in FIG. 4C, and the point at which the positive increase in flow output starts is dependent upon the compressibility of the solvent being pumped. Thus, as higher compressibility solvents are utilized, the point at which the positive pulse would begin is shifted to the right as illustrated in FIG. 4C. For a highly compressible solvent the flow positive pulse might begin at 67. For a less compressible solvent, the flow positive pulse might begin at 69, and for an even less compressible solvent the flow positive pulse might begin at 71 as illustrated in FIG. 4C. Thus, the flow rate at line 45 at the outlet of the pump 15 is dependent upon the compressibility of the fluid being pumped.

FIGS. 5A through 5C are plots like FIGS. 4A through 4C but illustrating a cam contour for the cams 47 and 49 which produces a flow negative pulse. With this cam contour the speed of rotation of the shaft 51 must be increased in the period of overlap (rather than decreased as in FIGS. 4A–4C embodiment) to compensate for the compressibility of the solvent and to maintain a constant flow output in the line 45.

It should be noted that the effect of solvent compressibility on the flow output is reversed in the FIGS. 5A through 5B embodiment as compared to the effect in the FIGS. 4A through 4C embodiment. The effect of the compressibility of the solvent upon the magnitude of the spike in the pulse output is also different. In FIG. 5C a highly compressible solvent 67 produces a large (negative) spike in the flow output, while in FIG. 4C a highly compressible solvent 67 produces a positive spike in the flow output which may under some conditions of pump operation be of less magnitude than the spike produced by a less compressible solvent.

The control circuit 57 (shown in FIG. 6) for controlling the speed of rotation of the pump 15 comprises two control loops.

The advantages of two control loops are discussed in detail in U.S. Pat. No. 4,352,636 referred to above and are summarized below.

The circuit 57 comprises a first control 71 which provides a fast response to changes in the pressure output of the pump 15.

The circuit 57 also comprises a control loop 73 which provides a slower response to the average motor speed of the stepper motor 55.

Figure 6:
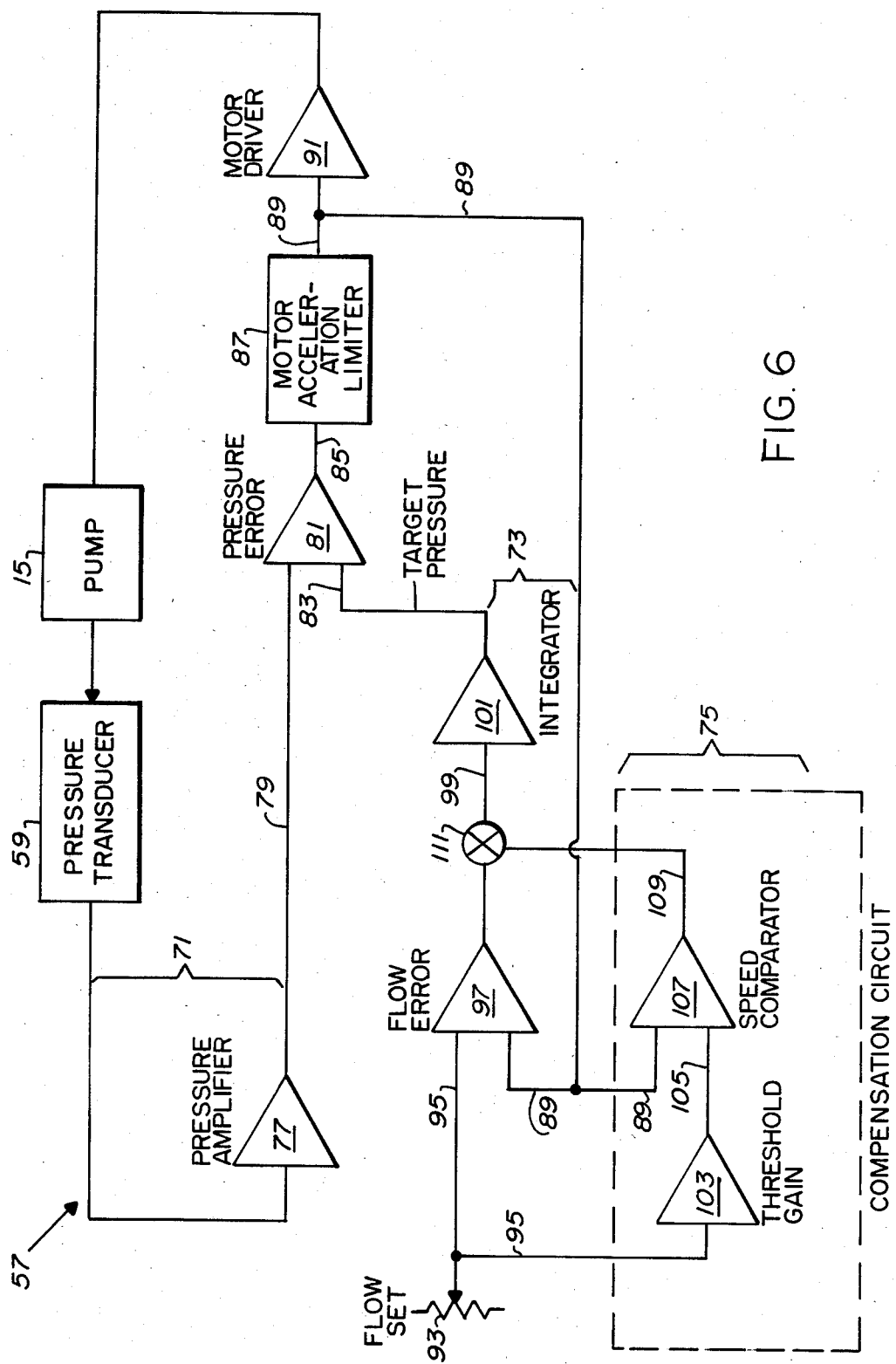

As illustrated in FIG. 6 the control circuit 57 also comprises a compensation circuit 75 which provides corrections for compressibility of the solvent.

The fast control loop 71 senses the pressure output of the pump 15 by means of the pressure transducer 59 and supplies a signal to an amplifier 77. The output signal of the pressure amplifier on the line 79 is compared (in a pressure error amplifier 81) to a target pressure signal on a line 83. The amplified difference between the signals on the line 79 and 83 is fed from the pressure error amplifier 81 on a line 85 to a motor acceleration limiter 87. This motor acceleration limiter 87 limits the swing of the signal to the capability of the stepper motor 55 for changing the speed of rotation of the shaft 51.

The output of the motor acceleration limiter 87 is then fed on a line 89 to a motor driver circuit 91, and this motor driver circuit 91 then drives the stepper motor 55 of the pump 15.

In a specific embodiment of the present invention the control loop 71 is an analog implemented control loop, but this control loop could also be a digital control loop.

The slow responding control loop 73 comprises a flow set point potentiometer 93 for setting the desired flow rate.

The signal from this potentiometer is conducted on a line 95 to a flow error amplifier 97, where it is compared with the average motor speed as transmitted on the line 89. The difference in the signals on the lines 95 and 89 is amplified by the flow error amplifier 97 and is transmitted on line 99 to an integrator 101.

The output of the integrator 101 constitutes a target pressure signal which is transmitted on the line 83 to the pressure error amplifier 81 as described above.

In operation, the output of the integrator 101 will slowly rise and the input will slowly change (either rising or falling) until the average input to the integrator 101 is zero. When the average input to the integrator 101 is zero, the integrator will produce an average target pressure output signal on the line 83.

If the time constant of the integrator 101 is long enough, the target pressure will be effectively constant throughout the entire cam cycle of the pump. In that event, the control effect would be too slow to provide effective control during a number of points of operation of the liquid chromotograph, such as, for example, initial start-up and changes in solvent composition.

In actual practice, the response of the integrator 101 must be fast enough to provide effective control for these occasions (e.g., initial start-up and during changes in solvent composition) in the operation of the liquid chromatograph.

FIGS. 7A and 7B illustrate the input to the integrator 101 when the integrator has reached a condition in which its average input is zero.

FIG. 7A illustrates the input for a solvent having a relatively low compressibility, and FIG. 7B illustrates the input for a solvent of different compressibility.

The input to the integrator 101 on the line 99 remains at a constant, known level 99A (see FIGS. 7A and 7B) during the time when the pump 15 is pumping without overlap between the pistons.

The input to the integrator 101 varies rapidly, and in a relatively unknown manner, during the time 99B (see FIGS. 7A and 7B) when the pistons are pumping in overlapping relationship.

During the time at which the input to the integrator 101 is at the level 99A, the flow is constant and known.

During the time that the input to the integrator 101 is illustrated by the pulse 99B, the flow is not constant and is not known exactly. The width of the pulse 99B is illustrated by $t_1$ in FIG. 7A and by $t_2$ in FIG. 7B.

The difference between the constant flow rate 99A and the desired flow rate 99C (representative of a input to the integrator) is indicated as $e_1$ in FIG. 7A and as $e_2$ in FIG. 7B.

The relationship of $e_1$ to $e_2$ is approximately proportional to the relationship of $t_1$ to $t_2$; hence, the difference between the desired flow rate 99C and the actual flow rate 99A is dependent upon the compressibility of the solvent. This is an undesirable situation from the standpoint point of maintaining effective accuracy of the flow rate.

As illustrated in FIG. 6 a compensation circuit 75 is associated with the slow control loop 73 both to compensate for the error presented by $e_1$ or $e_2$ in FIGS. 7A and 7B (which in practice is the error introduced by the variable compressibility of the solvent) and to selectively allow the use of a faster time constant for the integrator 101.

The compensation circuit 75 comprises a threshold gain amplifier 103. In a specific embodiment of the present invention the gain is set at about 0.75 to prevent hunting, and the amplifier 103 receives the flow rate set signal on the line 95 as set by the flow rate set potentiometer 93.

The output of the threshold gain amplifier 103 is supplied on a line 105 to the speed comparator amplifier 107.

The speed comparator amplifier 107 compares the instantaneous speed on line 89 with the set speed on line 105 and produces a control signal on line 109. This signal on line 109 controls a switch 111 which control signal on the line 99 to the integrator 101 to zero during the times represented by the pulses 99B shown in FIGS. 7A and 7B. That is, as soon as the beginning of a pulse 99B is sensed by the speed comparator 107, the speed comparator 107 forces the input to the integrator 101 to zero which forces the integrator 101 to hold a constant target pressure during this time. Thus, as illustrated in FIG. 8A, the input 99 to the integrator 101 increases rapidly in a spike or peak 113 as illustrated in FIG. 8A as at the beginning of the pulse illustrated as 99B in FIG. 7A, but the speed comparator 107 returns the input to the integrator back to zero (99C in FIG. 7A) on the line 99 in FIG. 6 as soon as this beginning of the pulse is detected. At the end of the pulse 99B as shown in FIG. 7, when the signal on the line 89 drops below the level of the signal on the 105, the speed comparator 107 (FIG. 6) reconnects the output of the error amplifier 97 to the integrator 101, and that causes the pulse 115 shown in FIG. 8A.

The effect of the compensation circuit 75 thus is to make the difference $e_3$ (see FIG. 8A) between the actual input to the integrator 101 and a zero input to the integrator 101 very small. Furthermore, this error is not as dependent on pulse width as the FIG. 7A mode of operation, and is in practical effect nearly independent of pulse width. Furthermore, the amounts of time represented by the areas beneath the spikes 113 and 115 are almost negligible so that the error is negligible in the operation of the pump, and the motor speed is an accurate reflection of pump flow.

The switch 111 thus forces the input to the integrator 101 to zero to force the integrator to hold the current target pressure at that point in the cycle of operation. The switch 111 is actuated in response to the sensing of the change in motor speed, and this results in pumping at the same target pressure existing at that time. Pumping at a constant pressure is, under these conditions of operation, equivalent to pumping at constant flow rate.

Since flow is substantially proportional to pressure for a given column and solvent, pumping at a constant pressure is an effective, short term, means of producing a constant flow during this overlap period of the two pump pistons 39 and 41.

Figure 10:
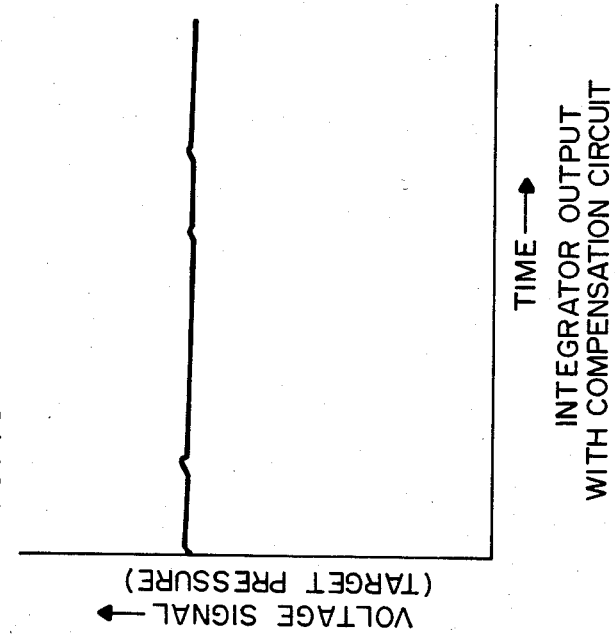
FIGS. 9 and 10 are diagrams illustrating the amplitude of the target pressure output signal of the integrator of the FIG. 6 circuit.
Figure 9:
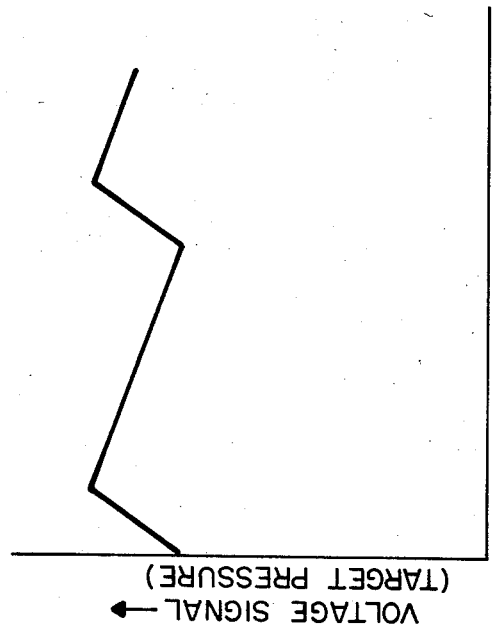

FIGS. 9 and 10 illustrate graphically the effective output of the integrator 101. In FIG. 9 the switch 111 passes the flow error signal from the amplifier 97 into the integrator 101 all the time. FIG. 10 illustrates the integrator 101 output with the switch 111 forcing the input to the integrator 101 to zero in response to the sensing of a flow pulse by the compensation circuit 75.

The amplitude of the integrator output signal is for an equivalent time constant integrator 101 in each of FIGS. 9 and 10. These FIGS. show that the variation in amplitude is less with the compensation circuit than it is without the compensation circuit. Therefore, a faster time constant can be used in the integrator for overcoming the problems of the slow loop response in startup and changing composition.

While we have illustrated and described the preferred embodiments of our invention, it is to be understood that these are capable of variation and modification, and we therefore do not wish to be limited to the precise details set forth, but desire to avail ourselves of such changes and alterations as fall within the purview of the following claims.

We claim:

1. A method of reducing pulsations in the flow produced by a multiple piston assembly pump of the kind which has a pressure piston assembly and a damper piston assembly connected in series with the outlet of the pressure piston assembly connected to the inlet of the damper piston assembly and which provides an overlap between the flow output of the piston assemblies during a portion of the strokes of the piston assemblies and wherein a sudden pump speed change occurs during the overlap between the flow output of the piston assemblies, said method comprising, controlling, except during the overlap, the speed of the pump by a first fast control loop which responds to pump output pressure and a second slow control loop which responds to average pump speed, detecting the sudden pump speed change which occurs during the overlap between the flow output of the piston assemblies, said step of detecting the speed change including detecting the beginning and the end of the actual duration of the time period of the overlap, and deactivating the slow control loop from controlling the pump speed during the time period of the overlap and running the pump to hold a substantially constant pump output pressure during the duration of the time period until the pump speed returns to the normal speed existing prior to the sudden speed change.

2. The invention defined in claim 1 wherein the first control loop includes a presure transducer connected to the outlet of the pump for transmitting a pressure signal to the first inlet of a pressure error amplifier and wherein the second control loop includes a flow error amplifier for producing an error signal representing the difference between the actual pump speed and a flow set point speed and wherein the second control loop also comprises an integrator for converting the flow error signal to a target pressure signal for input to a second input of the pressure error amplifier and including the steps of sensing the instantaneous speed of the pump, sensing the set point speed of the pump, comparing the instantaneous speed to the set point speed and supplying the difference to the integrator, and forcing the input to the integrator to zero in response to and during the duration of time involved between the detection of sudden pump speed change and the return to the normal pump speed.

3. A pump control for reducing pulsations in the flow produced by a multiple piston assembly pump of the kind which has a pressure piston assembly and a damper piston assembly connected in series with the outlet of the pressure piston assembly connected to the inlet of the damper piston assembly and which provides an overlap between the flow output of the piston assemblies during a portion of the strokes of the piston assemblies and wherein a sudden pump speed change occurs during the overlap between the flow output of the piston assemblies, said apparatus comprising, first relatively fast responding control loop means for controlling the speed of the pump in response to pump output pressure, second relatively slow responding control loop means for controlling the speed of the pump in response to average pump speed, compensation means for detecting the sudden pump speed change, including detecting means for detecting the beginning and the end of the actual duration of the time period of the overlap, deactivating means for deactivating the relatively slow responding control loop means and for running the pump to hold a substantially constant pump output pressure during the duration of the time period until the pump speed returns to the normal speed existing prior to the sudden speed change.

4. The invention defined in claim 3 wherein, the pump control includes a motor driver and a pressure error amplifier, the first control loop means include a pump output pressure transducer and a pressure amplifier connected to a first input of the pressure error amplifier, the second control loop means include a flow error amplifier having a first input which receives a flow set point signal and a second input which receives a pump instantaneous speed signal, an integrator, a line connecting the output of the flow error amplifier to the integrator, and switch means in said line for selectively disconnecting the integrator from the flow error amplifier, the output of the integrator is connected to a second input of the pressure error amplifier, and the compensation means activate the switch means at the beginning of the sudden pump speed change and deactivate the switch means on the return to the normal pump speed.

* * * * *

UNITED STATES PATENT AND TRADEMARK OFFICE
CERTIFICATE OF CORRECTION

PATENT NO. : 4,552,513

DATED : November 12, 1985

INVENTOR(S) : Leslie A. Miller et al

It is certified that error appears in the above-identified patent and that said Letters Patent are hereby corrected as shown below:

Column 6, line 27, "control" should read -- control loop --

Column 7, line 37, "input" should read -- zero input --

Column 7, line 66, "signal" should read -- control signal --

Column 7, line 66 and 67 "control signal" should read -- forces the input --

Signed and Sealed this

Twenty-fifth Day of February 1986

[SEAL]

Attest:

Attesting Officer

DONALD J. QUIGG

Commissioner of Patents and Trademarks